United States Patent [19]
Griffith

[11] Patent Number: 5,132,453
[45] Date of Patent: Jul. 21, 1992

[54] $N^6$-(HYDRAZINOIMINOMETHYL)LYSINE AND METHOD OF INHIBITING NITRIC OXIDE FORMATION IN BODY

[75] Inventor: Owen W. Griffith, New York, N.Y.

[73] Assignee: Cornell Research Foundation, Inc., Ithaca, N.Y.

[21] Appl. No.: 673,831

[22] Filed: Mar. 22, 1991

[51] Int. Cl.$^5$ .................................. C07C 241/00
[52] U.S. Cl. .............................. 562/560; 435/106; 435/240.31; 514/565
[58] Field of Search .......................... 562/560

[56] References Cited

U.S. PATENT DOCUMENTS

| | | | |
|---|---|---|---|
| 4,282,217 | 8/1981 | Baglioni | 514/179 |
| 4,698,442 | 10/1987 | Nestor et al. | 562/560 |
| 5,028,627 | 7/1991 | Kilbourn | 514/565 |
| 5,059,712 | 10/1991 | Griffith | 562/560 |

OTHER PUBLICATIONS

Fukuto, Biochem. Biophys. Res. Commun., 168 pp. 458–465.
Fasehun, O. A., et al., J. Pharmacol. Exp. Ther. 255, 1348–1358 (1990).
Greenstein, J. P., et al., Chemistry of Amino Acids, vol. 3, pp. 1850–1853, John Wiley & Sons, Inc., 1961.
Kilbourn, R., et al., (1990), in "Nitric Oxide from L-Arginine: A Bioregulatory System" (S. Moncada and E. A. Higgs, eds, pp. 61–67, Elsevier Science Publishers, Amsterdam).
Aisaka, K., et al., Biochemical and Biophysic Research Communications, vol. 160, No. 2, pp. 881–886, 4/28/89.
Iyengar, R., et al., Proc. Natl. Acad. Sci., U.S.A., vol. 84, pp. 6369–6373.
Palmer, R. M. J., et al., Nature (London), 333, pp. 664–666, 1988.
Rees, D. D., et al., Proc. Natl. Acad. Sci. U.S.A., vol. 86, pp. 3375–3378, 5/89.
Palmer, R. M. J., et al., Biochem and Biophysical Research Communications, 153, No. 3, 1251–1256 (6/88).
Steuhr, D. J., et al., The Journal of Immunology, 139, No. 2, 518–525, (1987).
Schmidt, H. H. H. W., et al., European Journal of Pharmacology, 154, 213–216, (1988).
Steuhr, D. J., et al., J. Exp. Med. vol. 169, pp. 1011–1020 (Mar. 1989).
Stuehr, D. J., et al., J. Biochem. and Biophysical Research Communications, vol. 161, No. 2, pp. 420–426 (6/15/89).
Turan, A., et al., Acta Chimica Academiae Scientiarum Hungaricae, Tomus 85 (3), pp. 327–332 (1975).
Kilbourn, R. G., et al., Proc. Natl. Acad. Sci. U.S.A. vol. 87, pp. 3629–3632, 5/90.
Sakuma, I., et al., Proc. Natl. Acad. Sci. U.S.A. vol. 85, pp. 8664–8667, 11/88.
Gross, S. S., et al., Biochemical and Biophysical Research Communications, vol. 170, No. 1, pp. 96–103, 7/16/90.
Natanson, C., et al., Journal of Exp. Med. 169:823–832 (1989).
Hibbs, J. B., et al., Biochem. Biophys. Res. Commun. 157:87–94(1988).
Marletta, M. A., et al., Biochemistry 27:8706–8711 (1988).
Palmer, R. M. J., et al., Nature 327:524–526 (1987).

Primary Examiner—Michael L. Shippen

[57] ABSTRACT

Physiologically active $N^6$-(hydrazinoiminomethyl)lysine or pharmaceutically acceptable acid addition salt thereof is administered in a nitric oxide sythesis inhibiting amount to a subject in need of such inhibition (e.g., a subject with low blood pressure, e.g., due to sepsis or to therapeutic administration of cytokines, or needing immunosuppressive effect) or is added to a medium containing isolated organs, intact cells, cell homogenates or tissue homogenates in an amount sufficient to inhibit nitric oxide formation to elucide or control the biosynthesis, metabolism or physiological role of nitric oxide. Compared to known nitric oxide synthesis inhibitors, $N^6$-(hydrazinoiminomethyl)lysine and its acid addition salts show a greater relative activity toward inducible isoform of nitric oxide synthase than toward constitutive isoform of nitric oxide synthase. $N^6$-(hydrazinoiminomethyl)lysine and its pharmaceutically acceptable acid addition salts are substantially less toxic than are $N^G$-amionoarginine and its pharmaceutically acceptable acid addition salts.

5 Claims, 3 Drawing Sheets

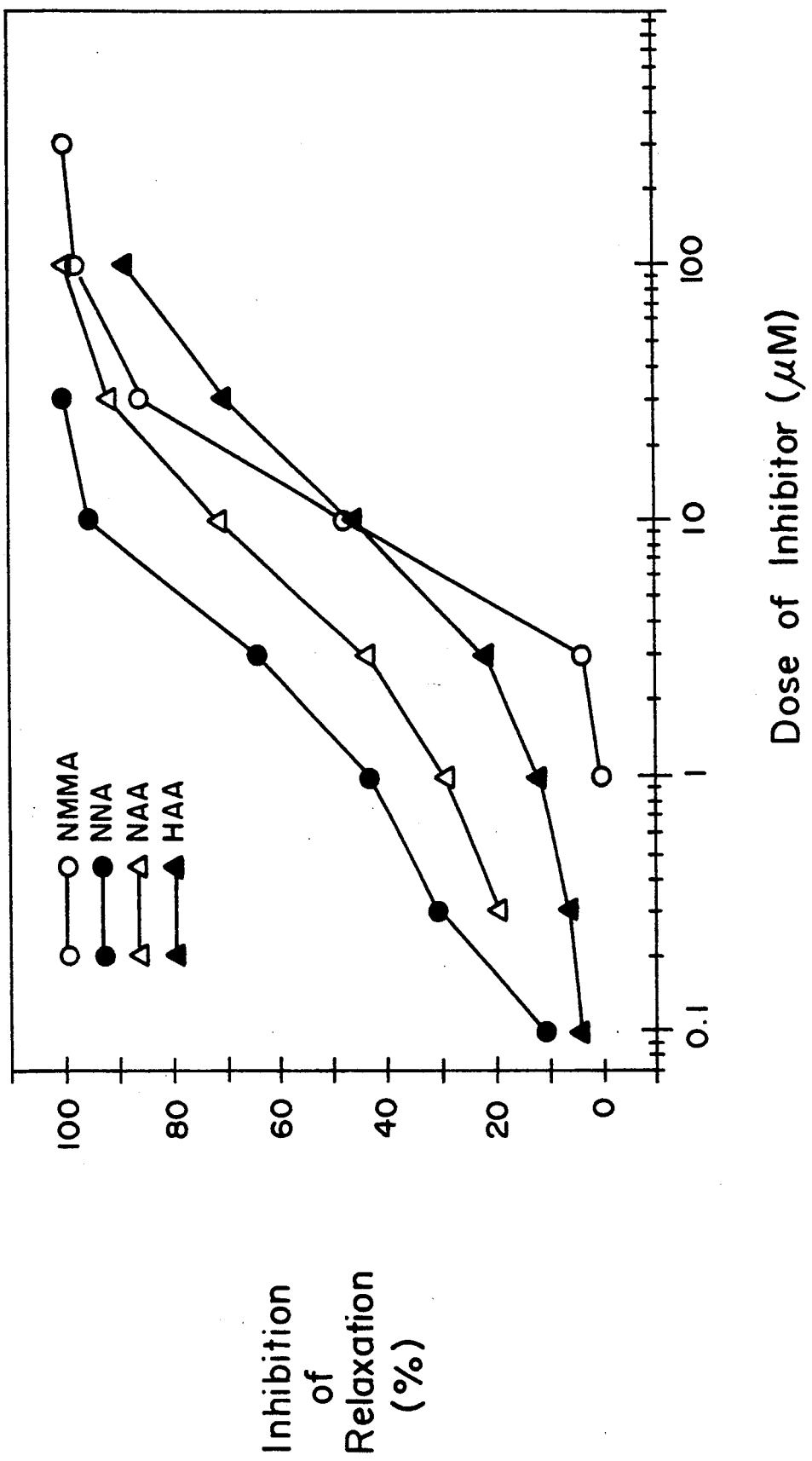

# N⁶-(HYDRAZINOIMINOMETHYL)LYSINE AND METHOD OF INHIBITING NITRIC OXIDE FORMATION IN BODY

This invention was made at least in part with Government support under National Institutes of Health grant number DK 37116. The Government has certain rights in the invention.

TECHNICAL FIELD

This invention is directed to novel inhibitors of biological nitric oxide formation.

BACKGROUND OF THE INVENTION

For several decades nitroglycerin has been administered to humans as a vasodilating agent in the treatment of cardiovascular disease. Recently, it has been shown that nitroglycerin so administered is converted in the body to nitric oxide which is the pharmacologically active metabolite. Still more recently, nitric oxide has been shown to be formed enzymatically from arginine as a normal metabolite which is an important component of endothelium-derived relaxing factors (EDRFs). EDRFs are currently being intensively studied as participating in regulation of blood flow and vascular resistance. In addition to vascular endothelium, macrophages have also been shown to produce nitric oxide in the body which is a component of their cell killing and/or cytostatic function (Iyengar, R., et al, Proc. Natl. Acad. Sci, USA, Vol. 84, pp. 6369-6373, September, 1987).

More recently it has been established that the enzyme forming nitric oxide from arginine, i.e., nitric oxide synthase, occurs in two distinct isoforms, namely the constitutive isoform and the inducible isoform. The constitutive isoform is present in normal endothelial cells, neurons and some other tissues. Formation of nitric oxide by the constitutive isoform in endothelial cells is thought to play a role in normal blood pressure regulation. The inducible isoform of nitric oxide synthase has been isolated from activated macrophages and is induced by various cytokines or combinations of cytokines in endothelial cells and vascular smooth muscle cells. It is thought that in sepsis or cytokine-induced shock that the observed life-threatening hypotension is due mainly or wholly to overproduction of nitric oxide by the inducible isoform of nitric oxide synthase. The specific tissue(s) responsible are not yet known but are likely to include endothelium and vascular smooth muscle.

Because of the physiological importance of the above, a search has been carried out for compounds which will block nitric oxide production in the body. The first compound discovered for use to obtain this effect is N$^G$-methyl-L-arginine (referred to herein as NMMA) (Palmer, R. M. J., et al, Nature (London), 333, pp. 664-666, 1988; Palmer, R. M. J., et al, Biochem. Biophys. Res. Commun. 153, pp. 1251-1256, 1988). Administration of NMMA to guinea pigs and rabbits has been shown to increase blood pressure (Aisaka, K., et al, Biochem. Biophys. Res. Commun. 160, No. 2, pp. 881-886, Apr. 28, 1989; Rees, D. D., et al, Proc. Natl. Acad. Sci. USA, Vol. 86, pp. 3375-3378, May, 1989). A second compound that has been discovered for use to obtain this effect is N$^G$-nitro-L-arginine (referred to herein as NNA). This compound, often used as its more soluble methyl ester, is a good inhibitor of the constitutive form of nitric oxide synthase but is less effective than NMMA as an inhibitor of the inducible isoform (S. S. Gross et al, Biochem. Biophys. Res. Commun. 170, pp. 96-103 (1990)). Still another inhibitor is N$^G$-amino-L-arginine (referred to as NAA). This compound and its use as an inhibitor are described in Griffith, U.S. patent application Ser. No. 07/406,897, now U.S. Pat. No. 5,059,712. NAA is an excellent inhibitor of both the constitutive and inducible isoforms of nitric oxide synthase and has been shown to reverse the severe hypotension observed in endotoxic shock and cytokine-induced shock in dogs. NAA, however, can show some toxicity when administered for the length of time necessary to fully control the hypotension of these conditions.

SUMMARY OF THE INVENTION

In a broad aspect, the instant invention is directed to inhibiting nitric oxide synthesis in a subject in need of such inhibition by administering agent which preferentially inhibits inducible isoform of nitric oxide synthase over constitutive isoform of nitric oxide synthase, in a nitric oxide synthesis inhibiting amount, to said subject.

It has been discovered herein that physiologically active N⁶-(hydrazinoiminomethyl)lysine and its pharmaceutically acceptable acid addition salts constitute superior inhibitors of nitric oxide synthesis in the body and are more selective than NMMA, NNA, and NAA in inhibiting the inducible isoform of nitric oxide synthase over the constitutive isoform of nitric oxide synthase and are substantially less toxic than NAA and its acid addition salts. The term N⁶-(hydrazinoiminomethyl)lysine means N⁶-(hydrazinoiminomethyl)lysine in free base form. The term physiologically active N⁶-(hydrazinoiminomethyl)lysine means N⁶-(hydrazinoiminomethyl)lysine containing L-enantiomer thereof; in other words, the L-enantiomer portion is physiologically active. Preferably, the physiologically active N⁶-(hydrazinoiminomethyl)lysine is constituted of from 50% to 100% L-enantiomer with any remainder being D-enantiomer, e.g., of 50% L-enantiomer and 50% D-enantiomer, very preferably of 100% L-enantiomer. The term pharmaceutically acceptable acid addition salts means those acid addition salts that are acceptable for pharmaceutical purposes.

For the uses set forth hereinafter, compositions containing more than 99% by weight (on a water-free basis) of agent selected from the group consisting of physiologically active N⁶-(hydrazinoiminomethyl)lysine and pharmaceutically acceptable acid addition salts thereof, are preferred.

A method herein for inhibiting nitric oxide synthesis in a subject in need of such inhibition comprises administering a nitric oxide synthesis inhibiting amount of agent selected from the group consisting of physiologically active N⁶-(hydrazinoiminomethyl)lysine and pharmaceutically acceptable acid addition salts thereof, to said subject. In an application of this method, said agent is administered to a subject who has or is at risk to have increased synthesis of nitric oxide by inducible isoform of nitric oxide synthase, and is administered to preferentially inhibit inducible isoform of nitric oxide synthase over constitutive isoform of nitric oxide synthase.

A method herein for blocking nitric oxide formation from arginine in in vitro studies including studies with isolated organs, intact cells, cell homogenates and tissue homogenates to elucidate or control the biosynthesis, metabolism or physiological role of nitric oxide comprises adding agent selected from the group consisting of physiologically active $N^6$-(hydrazinoiminomethyl)lysine and pharmaceutically acceptable acid addition salts thereof to a medium containing said organs, cells, or homogenates at a concentration sufficient to inhibit nitric oxide formation.

The term "subject" is used herein to mean any mammal, including humans, where nitric oxide formation from arginine occurs. The methods herein for use on subjects contemplate prophylactic use as well as curative use in therapy of an existing condition.

BRIEF DESCRIPTION OF THE DRAWINGS

FIG. 3 shows extent of inhibition of nitric oxide synthesis by constitutive enzyme isoform as a function of inhibitor concentration and depicts results of Example VI.

DETAILED DESCRIPTION

Figure 1:
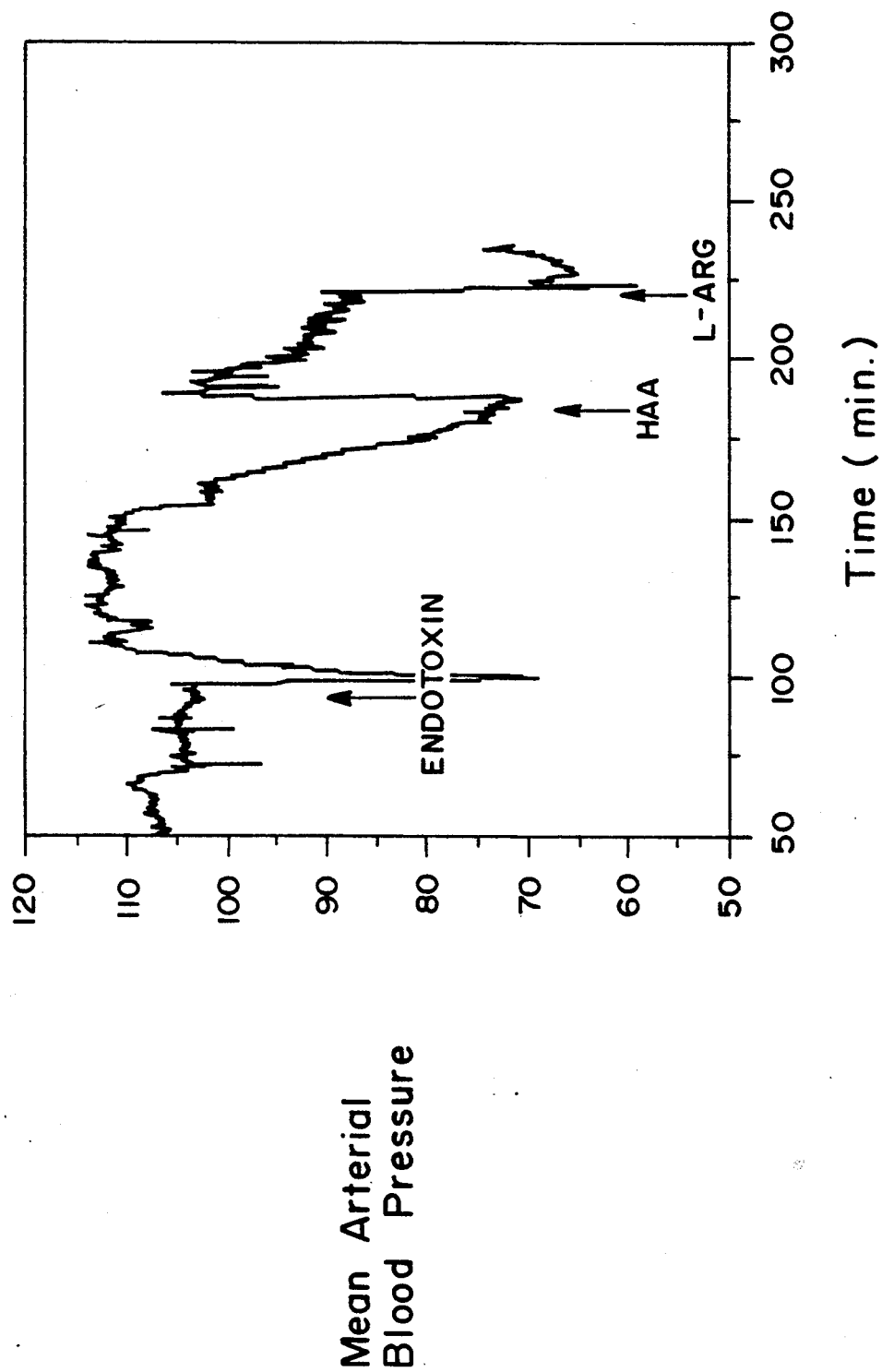
FIG. 1 shows the blood pressure tracing of a dog indicating the results of Example IV.

As previously indicated, inventive composition herein contains $N^6$-(hydrazinoiminomethyl)-L-lysine or a pharmaceutically acceptable acid addition salt thereof.

$N^6$-Hydrazinoiminomethyl)-L-lysine in the free base form has the structural formula:

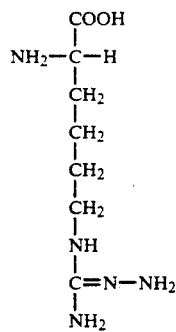

$N^6$-(Hydrazinoiminomethyl)-D,L-lysine in the free base form consists of 50% $N^6$-(hydrazinoiminomethyl)-L-lysine and 50% $N^6$-(hydrazinoiminomethyl)-D-lysine which has the structural formula:

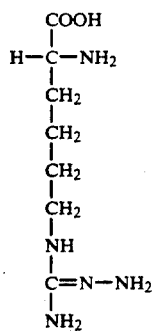

The pharmaceutically acceptable acid addition salts are formed initially at the nitrogen with the higher pKa and include, for example, the hydrochloric acid, sulfuric acid, acetic acid, gluconic acid, phosphoric acid, succinic acid, maleic acid, and citric acid addition salts. These are formed by methods well known in the art.

Acid addition salt of $N^6$-(hydrazinoiminomethyl)-L-lysine is readily prepared by a process comprising the following steps:

(a) reacting L-lysine with S-methylisothiosemicarbazide in aqueous solution at moderately alkaline pH to form $N^6$-(hydrazinoiminomethyl)-L-lysine;

(b) separating the $N^6$-(hydrazinoiminomethyl)-L-lysine from unreacted starting material by forming the insoluble flavianic acid salt of $N^6$-(hydrazinoiminomethyl)-L-lysine and isolating said salt;

(c) removing flavianate to form the free base by stirring a suspension of $N^6$-(hydrazinoiminomethyl)-L-lysine flavianate in water with strong base ion exchange resin (hydroxide form) and separating the flavianate containing resin;

(d) adding pharmaceutically acceptable acid to the resulting solution of $N^6$-(hydrazinoiminomethyl)-L-lysine to form the pH neutral acid addition salt;

(e) crystallizing said salt from aqueous alcohol and recovering said salt.

The D,L form is readily made as above except starting with D,L-lysine.

$N^6$-(hydrazinoiminomethyl)lysine of various percentages of L-enantiomer greater than 50% and less than 100% is readily prepared by admixing L-form and D,L-form in appropriate percentages.

We turn now to each of the steps of making in more detail.

We turn first to step (a). Both L-lysine and D,L-lysine are readily available from commercial sources. The S-methylisothiosemicarbazide is readily prepared by reacting thiosemicarbazide (commercially available) and methyl iodide; the general method is described in Tomcufcik, A. S., Chemical Abstracts, 72:90113c. A suitable reaction solvent in step (a) is water. The reaction is readily carried out at 25° C. to 100° C. at times ranging from 1 to 50 hours and at a pH ranging from 8-10. The product in step (a) is an aqueous solution of $N^6$-(hydrazinoiminomethyl)lysine and unreacted lysine.

In step (b), $N^6$-(hydrazinoiminomethyl)lysine is separated from unreacted lysine and inorganic salts by addition of inorganic acid to reduce the pH to about 7 and addition of flavianic acid in equimolar amount with the original lysine, to form $N^6$ -(hydrazinoiminomethyl)lysine flavianate, which is insoluble in water and separates. The separated material is readily purified, if necessary, by triturating with methanol and recrystallizing from water.

In step (c), the resin exchanges hydroxide for flavianate which is tightly bound to the resin. The hydroxide removes a proton from protonated $N^6$-(hydrazinoiminomethyl)lysine to form water and leave the $N^6$-(hydrazinoiminomethyl)lysine in the free base form. After separation of the resin, there remains a water solution of the $N^6$-(hydrazinoiminomethyl)lysine in the free base form, which can be used in suitably buffered systems in the methods herein.

In step (d), the pharmaceutically acceptable acid needed to make the acid addition salt is added to pH 7. Where the acid addition salt is desired, steps (c) and (d) are preferably carried out together by adding them in a manner such that the pH does not exceed 9.

For practical effecting of step (e), the product of step (d) is preferably first concentrated by rotary evaporation at reduced pressure.

Step (e) is readily carried out on concentrated product of step (d) by admixing with ethanol or methanol-ethanol mixtures whereby the acid salt of $N^6$-(hydrazinoiminomethyl)lysine crystallizes and is readily recovered by filtration.

$N^6$-(Hydrazinoiminomethyl)-L-lysine and acid addition salts thereof can also be prepared from L-homoarginine (commercially available) by the steps of nitration to form $N^G$-nitro-L-homoarginine and partial reduction of that compound to $N^6$-(hydrazinoiminomethyl)-L-lysine. The nitration is readily carried out utilizing a mixture of fuming nitric and fuming sulfuric acid (as described previously for L-arginine by Greenstein, J. P., et al, Chemistry of Amino Acids, Vol. 3, page 1852, John Wiley & Sons, Inc., 1961). The partial reduction is readily carried out by reaction of the formed $N^G$-nitro-L-homoarginine in solution with hydrogen gas in excess over a suitable reduction catalyst (e.g., Pt on charcoal, PtO, Pd on charcoal, and others well known in the reduction art). Suitable solvents are aqueous acids, e.g., 15% aqueous acetic acid. The reduction reaction is readily carried out at room temperature but temperatures ranging, for example, from 0° C. to 100° C. or higher can be employed. The reduction reaction proceeds readily at a pressure of 40 psi but can be carried out at pressures ranging from 1 to 2000 psi. The product is readily separated by ion exchange chromatography.

We turn now to the in vivo method herein, which comprises administering a nitric oxide synthesis inhibiting amount of agent selected from the group consisting of physiologically active $N^6$-(hydrazinoiminomethyl)lysine and addition salts hereof, to a subject in need of such inhibition.

One group of subjects comprises those with pathologically low blood pressure.

One class within this group are those with idiopathic hypotension.

Another class within this group are those with drug-induced hypotension, e.g., hypotension induced by administration of antitumor effective doses of cytokines such as tumor necrosis factor and interleukin-1. In this case coadministration pursuant to the method herein allows use of drugs that otherwise have unacceptable side effects.

Still another class within this group are those suffering from shock (including septic shock).

Reference is made to patent application Ser. No. 07/406,909, of Robert G. Kilbourn, Steven S. Gross, Owen W. Griffith and Roberto Levi titled "Inhibition of Systemic Hypotension Produced By Biologic Response Modifiers" filed on Sep. 13, 1989. The Kilbourn et al application embraces use of compounds including those claimed herein in inhibiting systemic hypotension.

Another group of subjects comprises those with immune disorders in which down regulation of nitric oxide formation is advantageous, e.g., in auto-immune disorders or in therapeutic immunosuppression for transplant purposes.

Turning now to dosage, such depends on the effect desired and the responsiveness of the individual subject. For example, for raising blood pressure, a blood pressure effective raising amount is administered. For disorders requiring immunosuppression, an immunosuppressive effective amount is administered. Generally, dosages for L-compound range from 10 micrograms per kg of body weight to 100 mg/kg of body weight, preferably 1 to 10 mg/kg of body weight, are useful. For the D,L-compounds, the dosage is twice that for L-compounds.

Administration may be carried out continuously or in single or multiple doses.

Administration is readily carried out, for example, by oral or parenteral (e.g. intravenous) routes.

The physiologically active $N^6$-(hydrazinoiminomethyl)lysine and pharmaceutically acceptable acid addition salts thereof are readily administered in combination with typical bulking agents, flavors and the like.

We turn now to the in vitro method herein. Typically, media include cardiac perfusion media, tissue culture media, incubation media used with cell or tissue homogenates or purified proteins. The organ treated is typically a blood vessel, lung or kidney. Intact cells include vascular endothelium or macrophages. The homogenates can be, for example, from cardiac, vascular, neural or other tissues and cells. The physiologically active $N^6$-(hydrazinoiminomethyl)lysine or salt thereof is added to the medium, in a concentration ranging from 1 nanomolar to 300 millimolar.

The invention is illustrated in the following examples.

EXAMPLE I 36.5 gm (0.2 mol) of L-lysine monohydrochloride was dissolved in 400 ml of 1M NaOH. To the clear solution was added 46.6 gm (0.2 mol) of S-methylisothiosemicarbazide monohydroiodide. The resulting solution, pH approximately 10, was heated at 70° C. with stirring for 7 hrs. At that time the reaction mixture contained approximately 57% of $N^6$-(hydrazinoiminomethyl)-L-lysine, 41% L-lysine and two minor by-products as judged by HPLC as indicated below. The reaction mixture was then neutralized to pH 7 by addition of concentrated HCl (about 13–15 ml) and cooled to 0° C. To the chilled, stirred solution was added a solution of flavianic acid (62.8 gm, 0.20 mol, in 100 ml of warm water) in several portions. A dark brown, gummy material formed and separated. The supernatant solution was decanted, and the residue was suspended in 150 ml of methanol. After stirring, a reddish-orange solid precipitated and was collected by filtration. The solid was washed with methanol (3×50 ml), ethanol (2×50 ml), and ethyl ether (2×50 ml). After drying several days under high vacuum, the crude $N^6$-(hydrazinoiminomethyl)-L-lysine flavianate (first crop) weighed 42.3 gm (0.082 mol, 41% yield). A second crop of 17.5 gm of crystalline material (0.034 mol, 17% yield) was obtained by chilling the aqueous solution decanted from the original gummy solid to 0° C.

The first crop material was stirred in 300 ml of boiling methanol for 5 minutes and then filtered hot. The solids were washed with hot methanol (3×50 ml), room temperature ethanol (2×50 ml), and ether (2×50 ml), and dried under high vacuum (weight=21.83 gm). The solids were then suspended in 200 ml of water, and the pH was raised to 7.5 by addition of 10M NaOH. The solids dissolved to give a deep orange solution. The pH was then lowered to 2.5 by addition of concentrated HCl, and $N^6$-(hydrazinoiminomethyl)-L-lysine flavianate was crystallized by chilling the mixture to 0° C. After 8 hours, the crystals were collected by filtration, and washed with methanol (3×50 ml), ethanol (2×50 ml), and ether (2×50 ml). The yield after drying under high vacuum was 16 gm of N⁶-(hydrazinoiminomethyl)-L-lysine flavinate (0.031 mol, 16% overall yield).

To remove flavianic acid and form the pharmacologically acceptable N⁶-(hydrazinoiminomethyl)-L-lysine monohydrochloride salt, 16 gm of the above product was suspended in 150 ml of water, and about 42 gm of air-dried Dowex-1 (200–400 mesh, strong base ion exchange resin, hydroxide form) was added slowly in small portions. The pH was carefully monitored, and the rate of addition was controlled to maintain the pH below 8.5. As the neutralization neared completion, concentrated HCl was added as required to maintain a pH between 7 and 8.5. After all of the ion exchange resin was added, the pH was adjusted with concentrated HCl to 7.0. The solution was then filtered to remove the resin (which neutralized and bound the flavianic acid), and the light brown filtrate was treated with 5 gm of acid-washed decolorizing charcoal. The charcoal was removed by filtration through Celite (diatomaceous earth filter material), and the colorless filtrate was reduced to about 10 ml by rotary evaporation at reduced pressure. To the resulting clear solution was added 100 ml of a solution containing 60 ml of methanol, 40 ml of ethanol, and 2 ml of water. As the resulting solution was slowly evaporated under reduced pressure (bath temperature about 10° C.), crystals of N⁶-(hydrazinoiminomethyl)-L-lysine monohydrochloride formed spontaneously. When the solution volume had been reduced to about 40 ml, the remaining solution was chilled to 0° C., and the crystals were collected by filtration. The crystals were washed with cold ethanol (3×25 ml) and ether. After drying under high vacuum over $P_2O_5$, the crystals weighed 7.0 gms (29 mmol, 15% overall yield, 36% yield from first crop material.

The final material was >99% pure HPLC (see below). $C_7H_{18}N_5O_2Cl$ requires: C=35.07%; H=7.58%; and N=29.22%. Found: C=35.40%; H=7.30%; and N=28.79%.

The purity of N⁶-(hydrazinoiminomethyl)-L-lysine was determined by reverse-phase HPLC on a 4.3×250 mm column of C-18 coated silica using a chiral solvent consisting of 8 mM cupric acetate and 17 mM L-proline pumped at 1 ml/min. (Gil-Av, E., Tishbee, A., and Hare, P. E. (1980) J. Am. Chem. Soc. 102, 5115–5117). Detection was made using an in-line fluorescence monitor after post-column derivatization with o-phthaldehyde solution pumped at 0.5 ml/min (Gil-Av, E. et al as above). In this system, L-lysine and N⁶-(hydrazinoiminomethyl)-L-lysine elute at 6.3 and 20 min., respectively.

EXAMPLE II

To test the toxicity of N⁶-(hydrazinoiminomethyl)-L-lysine, a 30 kg awake dog was administered the hydrochloride salt of the drug at a dose of 20 mg/kg body weight as a single intravenous (i.v.) bolus. There were no signs of toxicity and no increase in blood pressure. After 30 min., an additional dose of 20 mg/kg was given and an i.v. infusion of drug at a rate of 10 mg/kg body weight per hour was started. The infusion was continued 5 hours. The dog exhibited no significant change in blood pressure, showed no change in behavior, and did not vomit or exhibit disequilibrium. Twenty-four hours later the dog still appeared generally well but exhibited periodic isolated myoclonic muscle spasms which appeared to be painless to the dog. The spasms ended within 24 hours (48 hours after the experiment started), and the dog appeared normal and well in all respects.

An awake dog given the same dose of N$^G$-amino-L-arginine under similar circumstances experienced major seizures.

EXAMPLE III

To test the long-term toxicity of N⁶-(hydrazinoiminomethyl)-L-lysine, 0.209 ml of a 200 mM solution of the hydrochloride salt of the drug (48 mg/ml) was loaded into each of three Alzet Osmotic Pumps (Model 2001), and the pumps were implanted subcutaneously on the backs of three individual Swiss-Webster mice (wts. 30.7, 34.8 and 33.4 gms) under pentobarbital anesthesia. Each pump delivered the solution of drug at a rate of 0.92±0.05 µl/hour for 1 week. The mice showed no signs of toxicity and survived for >4 weeks; the experiment was then ended.

EXAMPLE IV

To test the efficacy of N⁶-(hydrazinoiminomethyl)-L-lysine, a 28 kg fasted dog was anesthetized with pentobarbital (25 mg/kg, i.v.), orotracheally intubated to allow ventilation with a Harvard pump, and instrumented to allow arterial blood pressure to be monitored via a central catheter. After a constant normal blood pressure had been observed for about 90 min., a solution containing 2 mg/kg body weight of endotoxin (*E. coli* lipopolysaccharide obtained from Sigma Chemical Co.) was given as an intravenous bolus injection. Blood pressure dropped rapidly a few minutes later and spontaneously recovered. Beginning at about 150 min. and continuing over the next 35 minutes, the dog became progressively hypotensive in a manner characteristic of septic (endotoxic) shock. When the mean arterial blood pressure had declined to about 70 mm Hg, a bolus intravenous injection of 20 mg/kg of N⁶-(hydrazinoiminomethyl)-L-lysine monohydrochloride (denote HAA) was given. The blood pressure increased by about 30 mm Hg within a few minutes and remained in a physiologically acceptable range for about 45 min. At that time, the dog was given a bolus intravenous injection of 400 mg/kg of L-arginine (denoted L-ARG), the substrate of nitric oxide synthase and a specific antagonist of nitric oxide synthase inhibitors competing for the L-arginine binding site. The blood pressure dropped precipitously to a level characteristic of septic (endotoxic) shock. Reversal by L-arginine established that the blood pressure increase seen with N⁶-(hydrazinoiminomethyl)-L-lysine was due to inhibition of nitric oxide synthase. The results of this Example are set forth in FIG. 1.

EXAMPLE V

Figure 2:
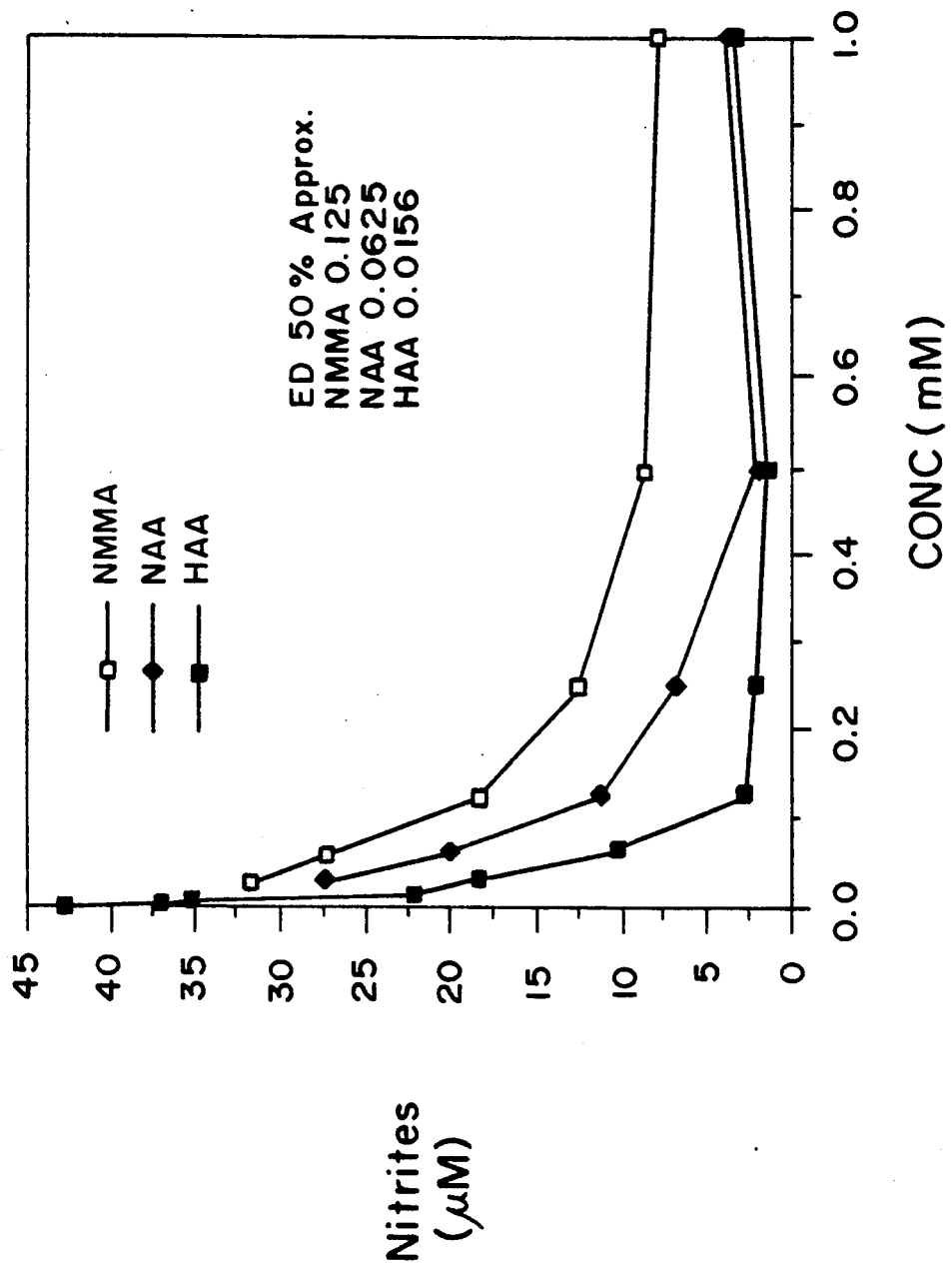
FIG. 2 shows extent of inhibition of nitric oxide synthesis by inducible enzyme isoform as measured by formation of nitrite as a function of inhibitor concentration and depicts results of Example V.

In vitro studies with cultured endothelial cells were carried out to test the efficacy of N⁶-(hydrazinoiminomethyl)-L-lysine as an inhibitor of the cytokine-induced nitric oxide synthase isozyme relative to established inhibitors. Cultured mouse brain endothelial cells were grown for 18 hrs. in the presence of 1000 units/ml of gamma-interferon and 5000 units/ml of tumor necrosis factor, conditions shown previously to cause enzyme induction (R. Kilbourn and P. Belloni (1990) in "Nitric Oxide from L-Arginine: A Bioregulatory System" (S. Moncada and E. A. Higgs, eds.) pp. 61–67, Elsevier Science Publishers, Amsterdam). For control cells the culture media contained 50% Dulbecco's Modified Eagle's Medium, 45% Ham's F12 Medium with 5% fetal calf serum. In the experimental groups, the culture media of the cells contained the constituents listed above and various concentrations of $N^6$-(hydrazinoiminomethyl)-L-lysine (HAA), $N^G$-methyl-L-arginine (NMMA), or $N^G$-amino-L-arginine (NAA). NMMA and NAA are previously described, well-characterized inhibitors of the inducible isozyme of nitric oxide synthase (Gross, S. S. et al. (1990) Biochem. Biophys. Res. Commun. 170, 96-103). Nitric oxide formation was monitored by following the increase in the concentration of nitrite in the culture medium. Nitric oxide spontaneously oxidizes to nitrite under the incubator conditions. The experimental results are shown in FIG. 2. As shown in FIG. 2, HAA is a substantially better inhibitor of the enzyme than is NAA or NMMA, the best competitive inhibitors previously identified. As indicated in FIG. 2, the doses required for approximately 50% inhibition (ED 50% approx.) were 0.125 millimolar for NMMA, 0.0625 millimolar for NAA and 0.0156 millimolar for HAA, indicating that HAA is approximately 4 times more potent than NAA and approximately 8 times more potent than NMMA.

EXAMPLE VI

In vitro studies with rat aortic rings were carried out to test the effect of $N^6$-(hydrazinoiminomethyl)-L-lysine relative to other known inhibitors of the constitutive isoform of nitric oxide synthase. Aortic rings (2-3 mm) were isolated, suspended under a resting tension of 2.00 gm in 5 ml glass chambers containing Krebs-Henseleit solution gassed with 95% $O_2$ and 5% $CO_2$ at 37° C. as described previously for vascular rings from guinea pigs (O. A. Fasehun et al, (1990) J. Pharmacol. Exp. Ther. 255, 1348-1353). The aortic rings were then contracted by addition of 0.03μM phenylephrine to the bathing solution, and the tension of the rings was measured. Acetylcholine, an agonist that stimulates the formation of nitric oxide by constitutive nitric oxide synthase in the vascular endothelium, was next added to a final concentration of 1 μM. The nitric oxide formed in response to acetylcholine causes the vascular smooth muscle of the aortic rings to relax, and the decrease in tension is measured. Inhibitors of nitric oxide synthase decrease the extent to which acetylcholine causes relaxation of the phenylephrine-contracted aortic rings. In the study, rings were contracted with phenylephrine, relaxed with acetylcholine, and then increasing doses of inhibitor were added to the bathing solution to overcome the effect of acetylcholine. The results are shown in FIG. 3. The dose of inhibitor is denoted on the X-axis. On the Y-axis, which is labeled "Inhibition of Relaxation (%)", 0% indicates the state where there is no inhibition of the relaxation caused by acetylcholine and 100% indicates the state of maximum constriction in response to inhibitor where the relaxant effect of acetylcholine has been completely overcome. Potency of inhibitors is typically compared on the basis of the concentration needed to overcome 50% of the relaxation caused by acetylcholine ($ED_{50}$). As indicated in FIG. 3, the $ED_{50}$'s for $N^G$-nitro-L-arginine (NNA), $N^G$-amino-L-arginine (NAA), $N^G$-methyl-L-arginine (NMMA) and $N^6$-(hydrazinoiminomethyl)-L-lysine (HAA) were determined to be about 1.5 μM, 4.2 μM, 10.2 μM, and 10.3 μM, respectively. This indicates that $N^6$-(hydrazinoiminomethyl)-L-lysine (HAA) is a much less effective inhibitor of the constitutive isoform of nitric oxide synthase than either NNA or NAA, and is comparable to NMMA. As shown in Example V, $N^6$-(hydrazinoiminomethyl)-L-lysine is much more effective than NMMA and NAA as an inhibitor of the inducible isoform of nitric oxide synthase. Of the compounds named, NNA is the least effective inhibitor of the inducible isoform (S. S. Gross et al (1990) Biochem. Biophys. Res. Commun. 170, 96-103).

When an equimolar amount of D,L-lysine is substituted for the L-lysine in Example I, pure $N^6$-(hydrazinoiminomethyl)-D,L-lysine monohydrochloride is obtained.

When in Examples IV and V, $N^6$-(hydrazinoiminomethyl)-D,L-lysine is substituted for $N^6$-(hydrazinoiminomethyl)-L-lysine in twice the dosage or concentration, substantially equal results of blood pressure increase and inhibition of nitrite formation by induced endothelial cells are obtained.

Many variations of inventive embodiments will be obvious to those skilled in the art. Thus, the invention is defined by the claims.

What is claimed is:

1. $N^6$-(hydrazinoiminomethyl)lysine containing L-enantiomer, or a pharmaceutically acceptable acid addition salt thereof.

2. The compound of claim 1 which is monohydrochloride acid addition salt of $N^6$-(hydrazinoiminomethyl)lysine.

3. The compound of claim 1 containing from 50% to 100% L-enantiomer with any remainder being D-enantiomer.

4. The compound of claim 3 which is 100% L-enantiomer.

5. The compound of claim 3 which is 50% L-enamtiomer and 50% D-enantiomer.

* * * * *

UNITED STATES PATENT AND TRADEMARK OFFICE
CERTIFICATE OF CORRECTION

PATENT NO. : 5,132,453

DATED : July 21, 1992

INVENTOR(S) : Owen W. Griffith

It is certified that error appears in the above-identified patent and that said Letters Patent is hereby corrected as shown below:

On the cover page under "OTHER PUBLICATIONS" add the date of --9/87-- at the end of the Iyengar et al citation.

Claim 5 (column 10, lines 49-50) change "L-enamtiomer" to --L-enantiomer--.

Signed and Sealed this

Fourteenth Day of September, 1993

*Attest:*

*Attesting Officer*

BRUCE LEHMAN

*Commissioner of Patents and Trademarks*